US00PP32617P2

(12) United States Plant Patent
Scorza et al.

(10) Patent No.: US PP32,617 P2
(45) Date of Patent: Dec. 15, 2020

(54) HARDY KIWI PLANT NAMED 'TANGO'

(50) Latin Name: ***Actinidia chinensis* Planch.**
Varietal Denomination: Tango

(71) Applicant: The United States of America, as Represented by the Secretary of Agriculture, Washington, DC (US)

(72) Inventors: Ralph Scorza, Shepherdstown, WV (US); Mark Demuth, Kearneysville, WV (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 16/501,886

(22) Filed: Jun. 26, 2019

(51) Int. Cl.
*A01H 5/08* (2018.01)
*A01H 6/00* (2018.01)

(52) U.S. Cl.
USPC ..... Plt./156
CPC ..... *A01H 6/00* (2018.05)

(58) Field of Classification Search
USPC ..... Plt./156
CPC ..... A01H 5/08
See application file for complete search history.

*Primary Examiner* — Kent L Bell
(74) *Attorney, Agent, or Firm* — John Fado; Ariel Atkinson

(57) ABSTRACT

A new hardy kiwi is of the variety denominated 'Tango' *Actinidia chinensis* Planch, originated from open pollination of *A. chinensis* selections collected in Rome. This new kiwi can be distinguished by its cold hardiness, high fruit quality, and relatively large fruit size.

10 Drawing Sheets

Latin name of the genus and species of the plant claimed: 'Tango' is a hardy kiwi that is an *Actinidia chinensis* Planch.

Variety denomination: The new hardy kiwi claimed is of the variety denominated 'Tango' *Actinidia chinensis* Planch.

BACKGROUND OF THE NEW PLANT

The present invention relates to the discovery of a new and distinct variety of kiwi known as *Actinidia chinensis* Planch., and here referred to as 'Tango' as herein described and illustrated. This new and distinct variety of kiwi vine produces fruit of high quality, of significantly larger size than the currently-grown cold hardy species such as *A. arguta* and *A. kolomikta*, and fruit of 'Tango' can be stored for extended periods.

This new and distinct variety of kiwi originated at the USDA-ARS Appalachian Fruit Research Station, Kearneysville, W. Va. from open pollination of *A. chinensis* selections collected by A. Nicotra, Istituto Sperimentale per la Frutticoltura, Rome. These original selections were produced from seeds collected in Guanxi province, China in 1988. One hundred and forty second generation seedlings that originated from seed collected from 19 vines grown in Rome were field planted at the USDA-ARS Appalachian Fruit Research Station, Kearneysville, W. Va. in 1995. Only two vines survived the cold winter temperatures between 1995 and 2015 with a recorded lowest temperature recorded during that period of −21° C. on Jan. 23, 2014 (FIG. 1).

SUMMARY OF THE NEW PLANT

'Tango' differs from its parents and other *Actinidia chinensis* in its combination of cold hardiness, high fruit quality, and relatively large fruit size. In addition, it can be stored for extended periods.

'Tango' was evaluated from 2002 through 2015 at one location, the USDA-ARS Appalachian Fruit Research Station (39.3629° N, 77.8633° W). This location is in USDA Plant Hardiness Zone 6a with predicted low weather extremes of −10 to −5° F. (−23.3 to −20.5° C.). 'Tango' grew vigorously, was untrained and received little pruning. No fruit thinning was practiced, and no supplemental irrigation was applied, nor was fertilizer or pesticides applied.

'Tango' fruited from 2002 through 2015 surviving winter temperatures as low as −6° F. (−21.1° C.) (FIG. 1). In 2004 fruit were harvested but yield data were not recorded. In 2012 the crop was reduced to a few fruits due to a severe spring frost event during bloom. Bloom of 'Tango' generally occurred between May 1 and May 15 at the test location and 'Tango' fruit were harvested usually at the first frost, between the third week in October and the first week of November. Over 12 years of fruit evaluation, fruit length averaged 4.3 cm, diameter 3.5 cm and weight 35.0 g. Brix as a measure of sweetness at harvest ranged from 7.2 to 15.4 (FIG. 3). Fruit flesh tends towards a green color, (yellow-green 144C, Royal Horticulture Society, London) at harvest. Fruit can be stored at 5° C. following harvest for extended periods up to 90 days.

'Tango' has been propagated from semi-hardwood cuttings using a modification of the method described by Sim and Lawes (1981). Cuttings were dipped in 3500 ppm IBA derived from Woods Rooting Compound (Earth Science Products, Aurora, Oreg.) and stuck into flats containing 70% potting mix (Metro-Mix 510, Sun Gro, Vancouver, Canada) and 30% coarse perlite. Flats were covered with a humidity dome and placed into a reach-in growth chamber (Conviron, Winnipeg, Canada) set for a 16 hour daylength at 20° C. with 70-80% relative humidity. Seventy percent rooting was achieved in 3 weeks.

BRIEF DESCRIPTION OF THE FIGURES

This new hardy kiwi plant is illustrated by the accompanying figures that show the flowers, fruit and entire plants.

the colors shown in the photographs are as true as can be reasonably obtained by conventional photographic procedures.

DETAILED DESCRIPTION OF THE NEW CULTIVAR

Figure 1:
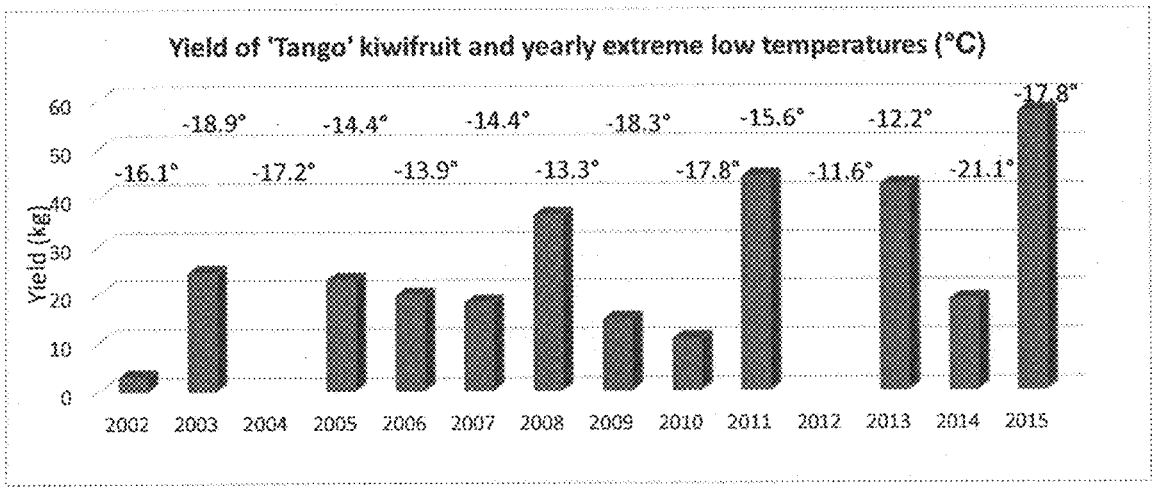
FIG. 1 shows the yield of 'Tango' kiwi fruit over a 14-year period. In 2004 fruit were harvested but yield data was not recorded. In 2012 the crop was reduced to a few fruit due to a severe frost event during bloom. Extreme low temperature dates in all years occurred between December 6 and February 24.
Figure 2:
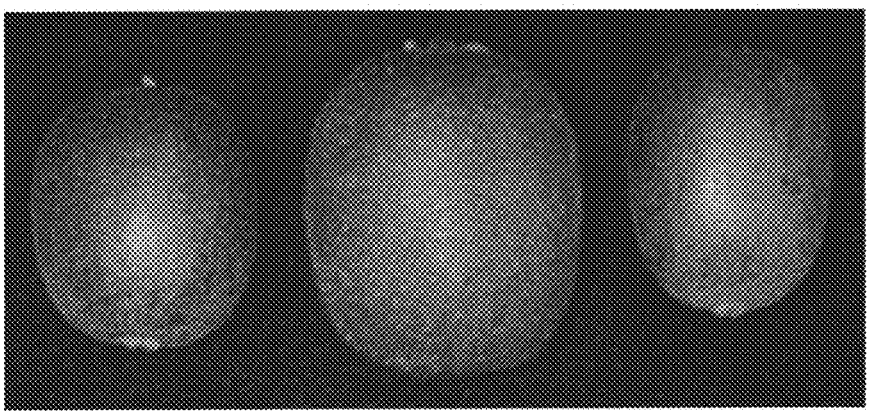
FIG. 2 shows a comparison of the fruit of *Actinidia chinensis* 'Tango' (left and right) with commercial kiwifruit *A. deliciosa* (middle).
Figure 3:
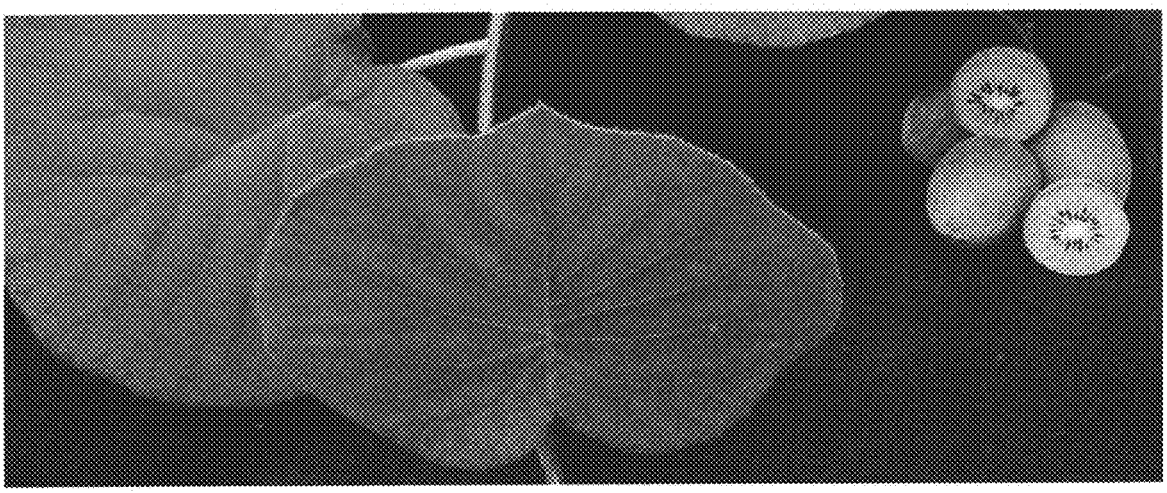
FIG. 3 shows 'Tango' plant fruit and foliage.
Figure 4:
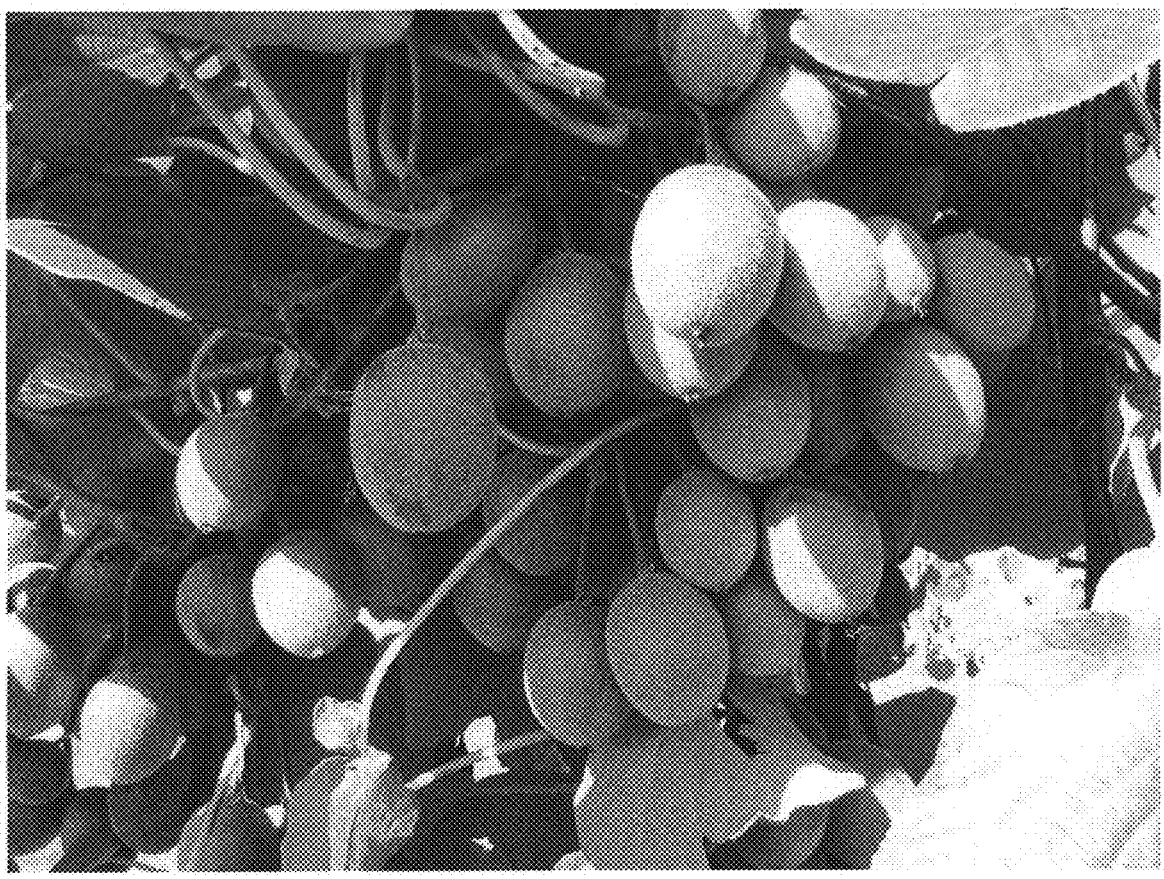
FIG. 4 shows 'Tango' fruit growing on the plant.
Figure 5A:
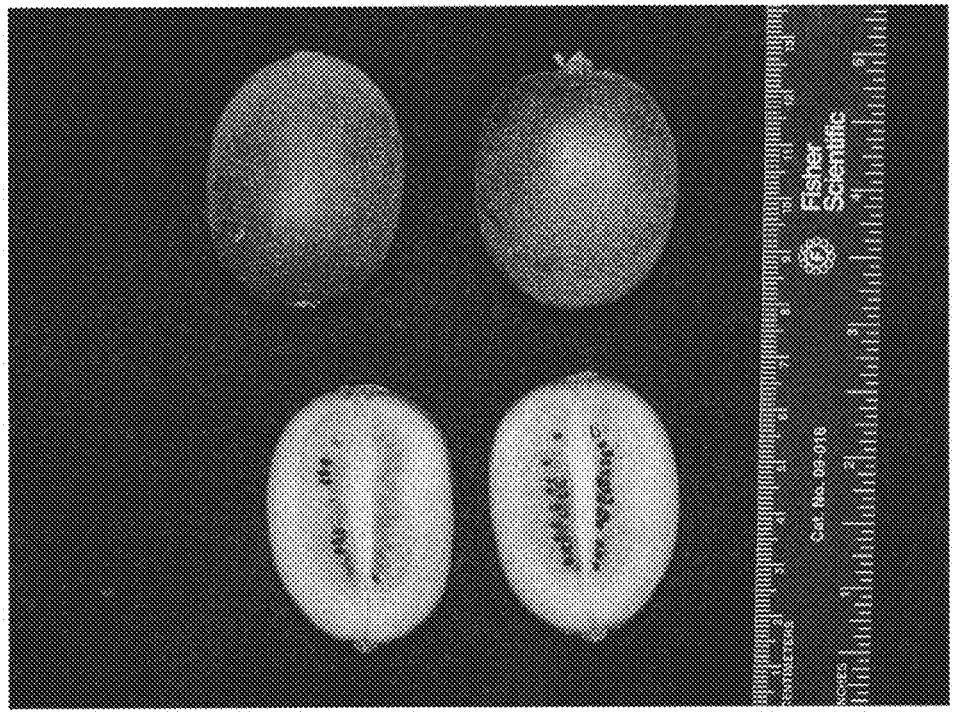
FIG. 5A and FIG. 5B show whole and cross-sectioned fruit of 'Tango' cut lengthwise (5A) and crosswise (5B).
Figure 5B:
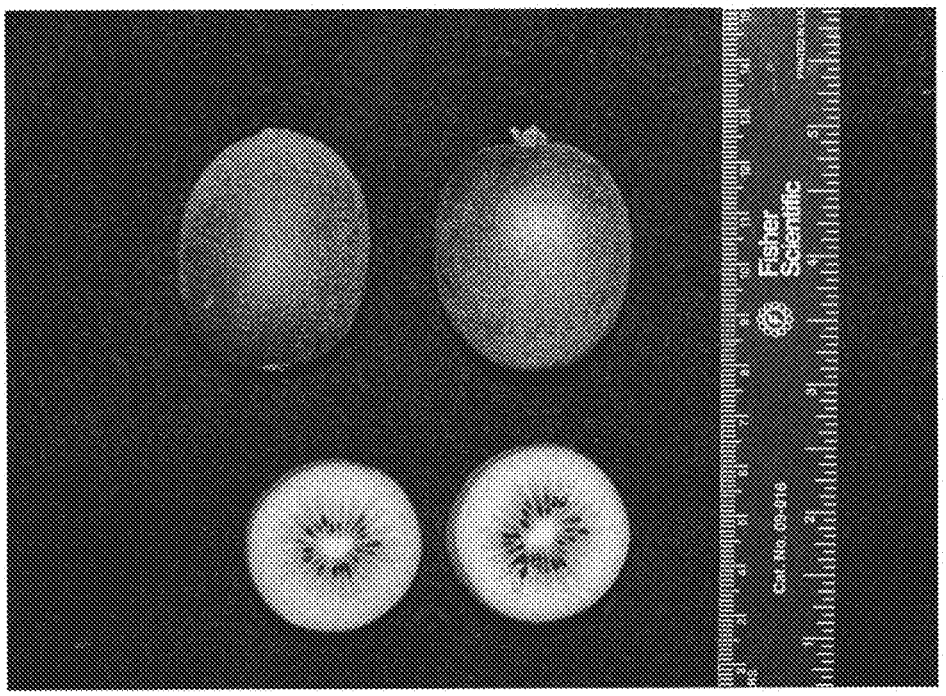
Figure 6:
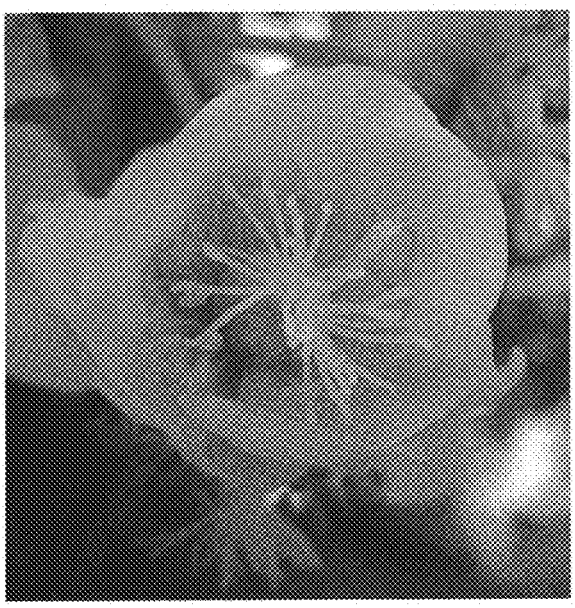
FIG. 6 shows a single flower of 'Tango' on the plant in the field.
Figure 7:
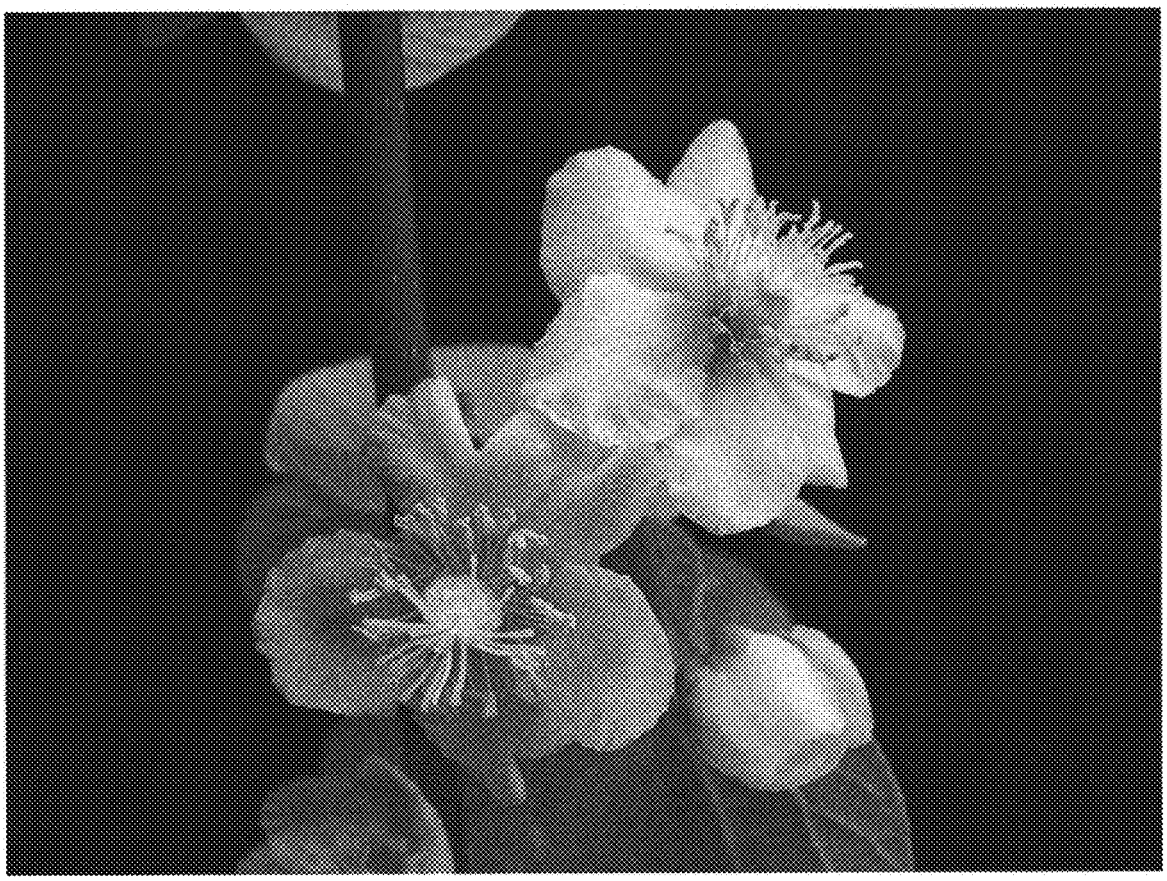
FIG. 7 shows open flowers and a flower bud of 'Tango' on a cutting taken in the lab.
Figure 8A:
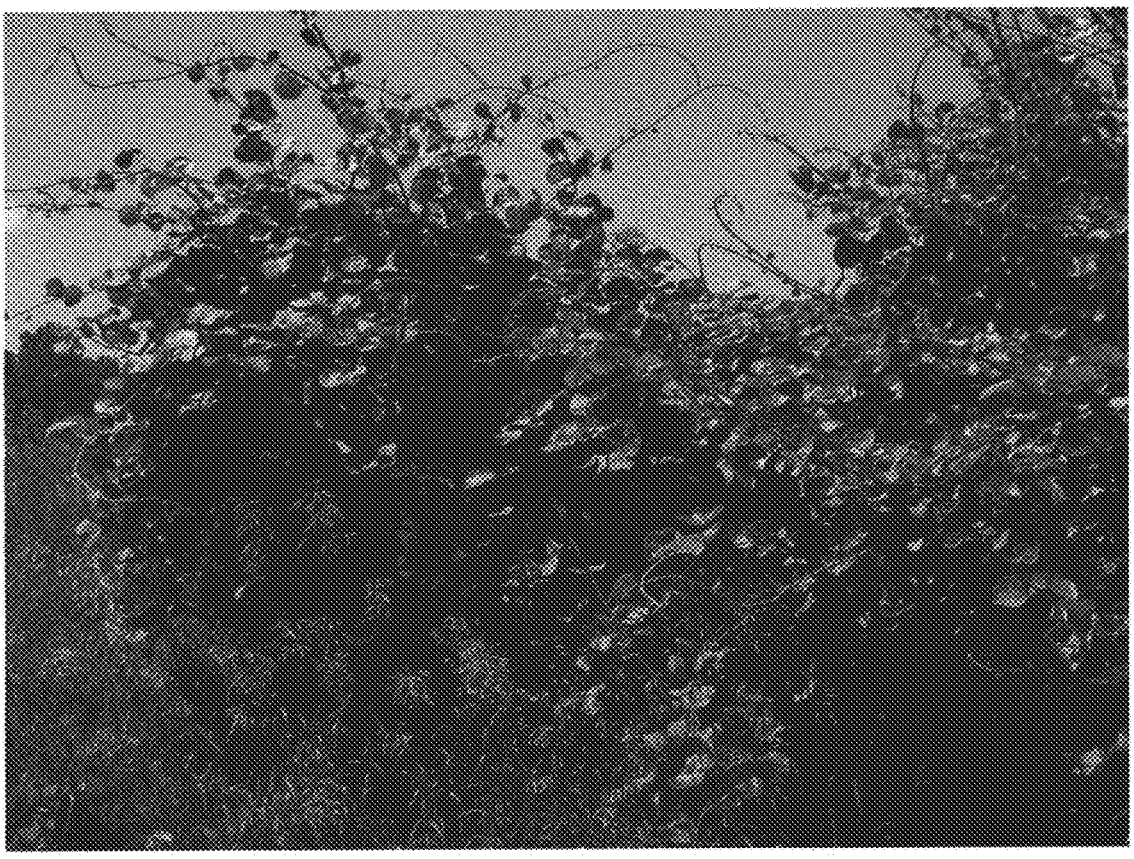
FIGS. 8A, 8B, and 8C show pictures of 'Tango' plants with full foliage in June of 2019.
Figure 8B:
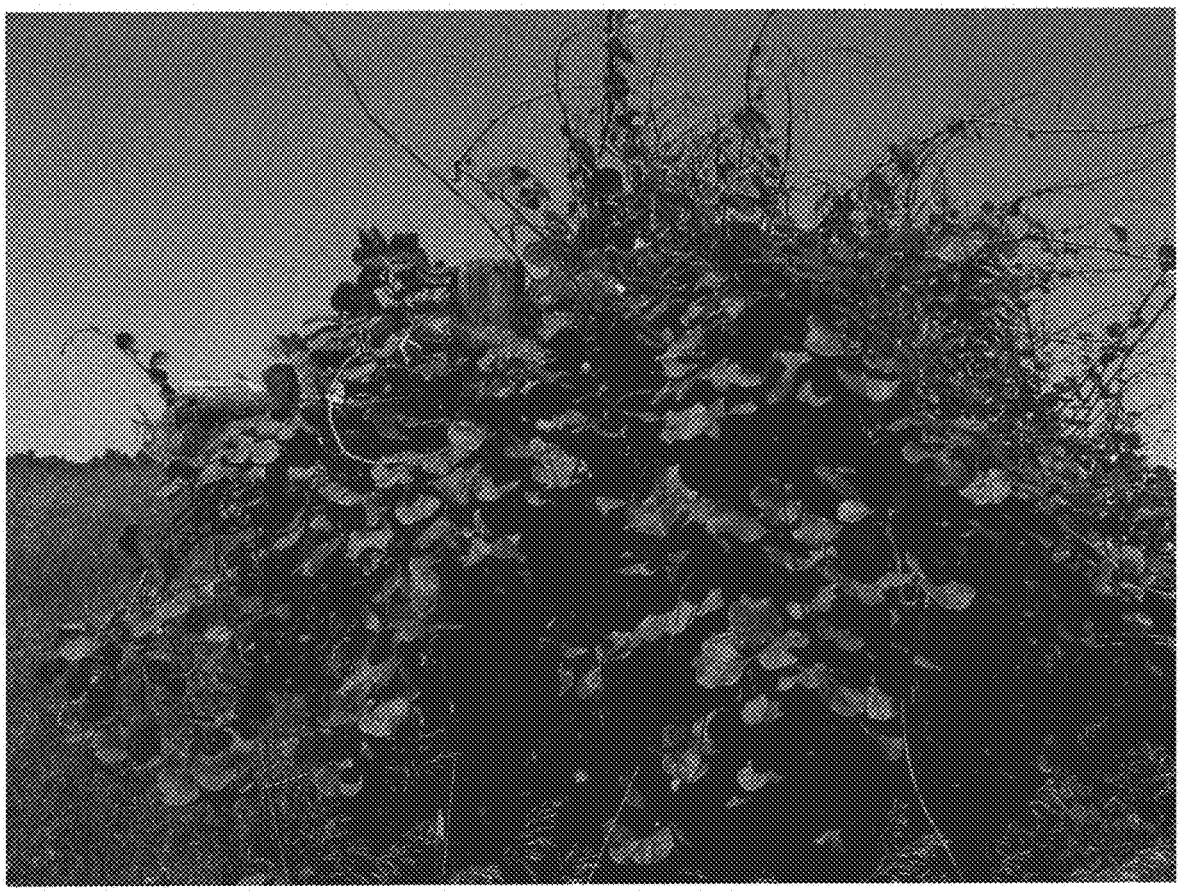
Figure 8C:
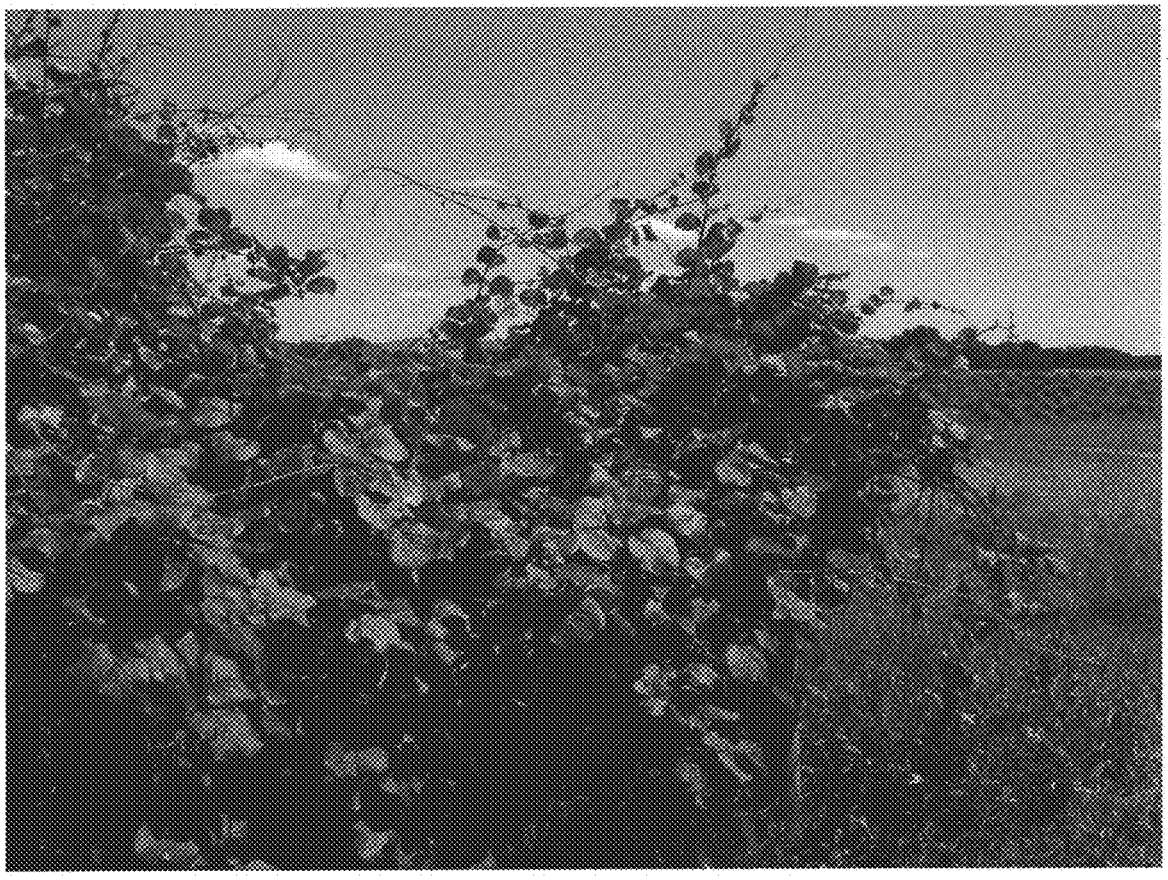

The following description of 'Tango' is based on observations taken over a 14-year evaluation period in Kearneysville, W. Va. This description is in accordance with UPOV terminology. Color designations, color descriptions and other phenotypical descriptions may deviate from the stated values and descriptions depending upon variation in environmental, seasonal, climatic and cultural conditions. 'Tango' has not been observed under all possible environmental conditions. Color terminology follows The Royal Horticultural Society Colour Chart. London (R.H.S. 4$^{th}$ Ed., 2001).

Leaf color:
- *Adaxial*.—Mostly green group 141A, some areas 141B.
- *Abaxial*.—Mostly greyed-green group 191A, some areas 191B.

Leaf vein color:
- *Adaxial*.—Yellow-green 153D.
- *Abaxial*.—Greyed-yellow 160C, covered in fine pubescence green-white 157B. Large veins often traced with pubescence of greyed-orange 164C.

Petiole color: Greyed green 193B, covered in fine pubescence greyed-orange N170D on sun exposed surface, greyed-orange N167C on shaded surface.

Petiole:
- *Length* (*mm*).—109.2.
- *Width* (*mm*).—3.9.

Leaf shape: Broadly cordate.
- *Apex*.—Acuminate, occasionally obcordate.
- *Base*.—Cordate.
- *Margin*.—Ciliate.

Leaf surface:
- *Adaxial*.—Glabrous.
- *Abaxial*.—Tomentose.

Leaf blade size:
- *Length* (*mm*).—123.9.
- *Width* (*mm*).—140.8.
- *Thickness* (*mm*).—0.44.
- *Area* ($mm^2$).—14377.0.

Inflorescence: Solitary, very rarely cymes.

Flower diameter: (mm) 35.5. Flowers are fragrant.

Petal shape: Broadly ovate.

Petal color:
- *Adaxial*.—White 155C. base of petal white 155A, 144C at point of attachment.
- *Abaxial*.—White 155C, base of petal yellow-green 144C at point of attachment. Petals become orange 25 C at petal fall.

Petal size (mm):
- *Length*.—18.7.
- *Width*.—17.3.

Petal number: 6.

Calyx: Sepals cupped.

Sepal color: Green 138D, margins and apex grey-orange N167A becoming greyed-brown 199D at fruit maturity.

Sepal size (mm):
- *Length*.—7.8.
- *Width*.—5.4.
- *Number*.—6.

Pedicle color: Yellow-green 145C, becoming greyed-brown 199A at fruit maturity.

Pedicle size (mm):
- *Length*.—31.6.
- *Diameter*.—1.3.

Stigma:
- *Stigma color*.—White 155C.
- *Stigma numbers*.—27.
- *Stigma size*.—Diameter (mm) 0.33.

Style:
- *Style numbers*.—27.
- *Style size* (*mm*).—Length 5.7. Diameter 0.33.

Anther:
- *Anther color*.—Yellow-orange 11A, occasionally 17D. Becoming yellow-orange 14A at petal fall.
- *Anther size* (*mm*).—Length 2.2. Diameter 1.1.

Filament:
- *Filament color*.—White, 155C, becoming green 144C at base.
- *Filament length* (*mm*).—6.9.

Pollen: Yellow 8D, non-viable.

Ovary:
- *Ovary color*.—White N155C, covered with pubescence white N155D.
- *Ovary size* (*mm*).—Length 5.5. Length 5.7.

Fruit:

Skin color: mostly yellow-green 144B, some areas yellow-green 144A. Skin covered in fine downy pubescence of greyed-orange 165B.

Lenticels: Abundant, small, greyed-orange 164B.

Lenticel density: 3.9/$cm^2$.

Fruit color:
- *Flesh*.—Outer pericarp yellow-green 144C with rays of yellow-green 144D. Inner pericarp: yellow-green 144B.
- *Core*.—Yellow-green 144D.
- *Seeds*.—Mature seeds are brown group 200D, some are brown 200C. Less mature seeds are greyed-orange 165A.

Fruit size (mm):
- *Length*.—43.
- *Diameter*.—35.

Fruit weight (g): 35.

Fruit quality: At harvest ° brix as a measure of sweetness ranged from 7.6 to 15.4 from years 2002 to 2015.

Seed: Elliptical, glossy, entire surface is dimpled.

Seed size (mm):

*Length.*—2.3.

*Width.*—1.3.

*Thickness.*—0.9.

Seed weight (g): 0.019 per 15 seeds.

Vigor: Moderately vigorous to vigorous.

Shoot:

*Length (m) end of growing season.*—1.8.

*Caliper (mm).*—9.5.

Color: Yellow-green 144B, becoming greyed-orange 174A on sun exposed surfaces. Covered in dense hairs of greyed-orange N176B. 1-year-old shoots are greyed-orange 165A.

Lenticels:

*Length (mm).*—2.3.

*Width (mm).*—0.44.

*Density.*—(0.5 $cm^2$) 3.86.

*Color.*—Greyed-brown 199C.

Trunk: Bark, becoming very rough with by year 5.

*Bark color.*—2-year-old wood brown 200A, some areas of brown. 3-year-old wood brown N200A. >5-year-old wood brown N200B, some areas brown 201B.

COMPARISON WITH COMMERCIAL CULTIVARS

The size of the fruit of 'Tango' (length 4.3 cm, diameter 3.5 cm and weight 35.0 g) compares with commercially produced 'Hayward' (*Actinidia deliciosa*) measuring 7 cm in length and 5 cm in diameter, and 85-115 g weight (Cruz-Castillo et al., 1999; Minchin et al. 2010); with A. chinensis 'Hort16A' (ZESPRI™ GOLD), 76-84 inm in length, width 47-55 mm, weight 43-176 g (U.S. Plant Pat. No. 11,066); and with grape-sized cold hardy *A. arguta* with fruit weight of 5-12 g (Kepler and Kabaluk, 1995; Pescie and Strik, 2004; Williams et al., 2003). Fruit yield of 'Tango' averaged 25.7 kg/year over the 12-year fruiting test period (FIG. 1) compared with a recorded yield of 32.5 kg/vine for unthinned *A. arguta* (Pescie and Strik, 2004).

'Tango' differs from its parents and other *Actinidia chinensis* in its combination of cold hardiness, high fruit quality, and relatively large fruit size. In addition, it can be stored for extended periods.

We claim:

1. A new and distinct cultivar of hardy kiwi plant, substantially as illustrated and described, characterized by its cold hardiness, high fruit quality, and relatively large fruit size.

* * * * *